United States Patent
Gross et al.

(10) Patent No.: US 9,056,150 B2
(45) Date of Patent: Jun. 16, 2015

(54) COMPOSITIONS FOR TREATING BONE DEFECTS

(75) Inventors: Jeffrey M. Gross, Vancouver (CA); Steve Peckham, Memphis, TN (US); Jeffrey Scifert, Arlington, TN (US); Jeffrey Badura, Cordova, TN (US); Nelson Scarborough, Germantown, TN (US); Scott Vickers, Hernando, MS (US)

(73) Assignee: Warsaw Orthopedic, Inc., Warsaw, IN (US)

(*) Notice: Subject to any disclaimer, the term of this patent is extended or adjusted under 35 U.S.C. 154(b) by 1460 days.

(21) Appl. No.: 11/949,990

(22) Filed: Dec. 4, 2007

(65) Prior Publication Data

US 2009/0142385 A1  Jun. 4, 2009

(51) Int. Cl.
| | |
|---|---|
| A61F 2/28 | (2006.01) |
| A61K 38/17 | (2006.01) |
| A61K 33/06 | (2006.01) |
| A61P 19/00 | (2006.01) |
| A61L 27/46 | (2006.01) |
| A61L 27/48 | (2006.01) |
| A61L 27/54 | (2006.01) |
| A61K 38/00 | (2006.01) |

(52) U.S. Cl.
CPC ............ *A61L 27/46* (2013.01); *A61K 38/00* (2013.01); *A61L 27/48* (2013.01); *A61L 27/54* (2013.01); *A61L 2300/414* (2013.01); *A61L 2300/602* (2013.01)

(58) Field of Classification Search
None
See application file for complete search history.

(56) References Cited

U.S. PATENT DOCUMENTS

| | | | |
|---|---|---|---|
| 4,394,370 A | 7/1983 | Jefferies | |
| 4,430,760 A | 2/1984 | Smestad | |
| 4,440,750 A | 4/1984 | Glowacki et al. | |
| 4,472,840 A | 9/1984 | Jefferies | |
| 4,485,097 A | 11/1984 | Bell | |
| 4,722,948 A | 2/1988 | Sanderson | |
| 4,743,257 A * | 5/1988 | Tormala et al. | ............ 623/23.58 |
| 4,776,890 A | 10/1988 | Chu | |
| 4,789,663 A | 12/1988 | Wallace et al. | |
| 4,863,732 A | 9/1989 | Nathan et al. | |
| 5,162,114 A | 11/1992 | Kuberasampath et al. | |
| 5,275,954 A | 1/1994 | Wolfinbarger et al. | |
| 5,284,655 A | 2/1994 | Bogdansky et al. | |
| 5,290,558 A | 3/1994 | O'Leary et al. | |
| 5,298,254 A | 3/1994 | Prewett et al. | |
| 5,314,476 A | 5/1994 | Prewett et al. | |
| 5,356,629 A | 10/1994 | Sander et al. | |
| 5,405,390 A | 4/1995 | O'Leary et al. | |
| 5,439,684 A | 8/1995 | Prewett et al. | |
| 5,510,396 A | 4/1996 | Prewett et al. | |
| 5,513,662 A | 5/1996 | Morse et al. | |
| 5,516,532 A | 5/1996 | Atala et al. | |
| 5,531,791 A | 7/1996 | Wolfinbarger, Jr. | |
| 5,707,962 A | 1/1998 | Chen et al. | |
| 5,711,957 A | 1/1998 | Patat et al. | |
| 5,739,286 A | 4/1998 | Silver et al. | |
| 5,741,261 A * | 4/1998 | Moskovitz et al. | ............ 606/79 |
| 5,948,426 A | 9/1999 | Jefferies | |
| 6,030,635 A | 2/2000 | Gertzman et al. | |
| 6,124,273 A | 9/2000 | Drohan et al. | |
| 6,165,487 A | 12/2000 | Ashkar et al. | |
| 6,180,606 B1 | 1/2001 | Chen et al. | |
| 6,197,325 B1 | 3/2001 | MacPhee et al. | |
| 6,200,606 B1 | 3/2001 | Peterson et al. | |
| 6,214,368 B1 | 4/2001 | Lee et al. | |
| 6,281,195 B1 | 8/2001 | Rueger et al. | |
| 6,287,341 B1 | 9/2001 | Lee et al. | |
| 6,293,970 B1 | 9/2001 | Wolfinbarger, Jr. et al. | |
| 6,294,187 B1 | 9/2001 | Boyce et al. | |
| 6,297,213 B1 | 10/2001 | Oppermann et al. | |
| 6,309,659 B1 | 10/2001 | Clokie | |
| 6,311,690 B1 | 11/2001 | Jefferies | |
| 6,326,018 B1 | 12/2001 | Gertzman et al. | |
| 6,328,765 B1 | 12/2001 | Hardwick et al. | |
| 6,331,312 B1 | 12/2001 | Lee et al. | |
| 6,340,477 B1 | 1/2002 | Anderson | |
| 6,346,515 B1 | 2/2002 | Pitaru et al. | |

(Continued)

FOREIGN PATENT DOCUMENTS

| | | |
|---|---|---|
| WO | WO0236147 A1 | 5/2002 |
| WO | WO2005004755 A1 | 1/2005 |
| WO | WO2007090180 A1 | 8/2007 |

OTHER PUBLICATIONS

Oda et al. Ectopic Bone Formation by Biphasic Calcium Phosphate (BCP) combined with Recombinant Human Bone Morphogenetic Protein-2 (rhBMP-2) J Med Dent Sci. Sep. 1997; 44(3): abstract.*
Oda et al. Ectopic Bone Formation by Biphasic Calcium Phosphate (BCP) combined with Recombinant Human Bone Morhphogenic Protein-2 (rhBMP-2) J Med Dent Sci. Sep. 1997; 44 (3): abstract.*

*Primary Examiner* — Robert A Wax
*Assistant Examiner* — Danah Al-Awadi
(74) *Attorney, Agent, or Firm* — Sorell Lenna & Schmidt LLP

(57) ABSTRACT

In certain described embodiments, implantable medical materials comprise a scaffolding material, a liquid organic binder, and entrapped calcium-containing particles. The medical materials can incorporate an osteoinductive factor such as a protein. The scaffolding material can bind the factor. In additional described embodiments, implantable medical materials include an osteoconductive scaffolding material, an incorporated osteoinductive factor, and a biodegradable barrier material effective to delay release of the factor from the scaffolding material. The scaffolding material can bind the factor. Also described a methods for preparing and implanting the described medical materials.

25 Claims, 1 Drawing Sheet

(56) References Cited

U.S. PATENT DOCUMENTS

| | | |
|---|---|---|
| 6,368,356 B1 | 4/2002 | Zhong et al. |
| 6,372,257 B1 | 4/2002 | Marchosky |
| 6,375,663 B1 * | 4/2002 | Ebner et al. .................. 606/170 |
| 6,437,018 B1 | 8/2002 | Gertzman et al. |
| 6,458,375 B1 | 10/2002 | Gertzman et al. |
| 6,679,918 B1 | 1/2004 | Benedict et al. |
| 7,799,754 B2 * | 9/2010 | Hart et al. ...................... 514/8.2 |
| 7,838,022 B2 * | 11/2010 | Drapeau et al. ............... 424/423 |
| 2001/0014667 A1 | 8/2001 | Chen et al. |
| 2001/0018614 A1 | 8/2001 | Bianchi |
| 2002/0018796 A1 | 2/2002 | Wironen |
| 2002/0034531 A1 | 3/2002 | Clokie |
| 2002/0071827 A1 | 6/2002 | Petersen et al. |
| 2002/0072804 A1 | 6/2002 | Donda |
| 2002/0076429 A1 | 6/2002 | Wironen et al. |
| 2002/0082694 A1 | 6/2002 | McKay |
| 2002/0082697 A1 | 6/2002 | Damien |
| 2002/0098222 A1 | 7/2002 | Wironen et al. |
| 2002/0151985 A1 | 10/2002 | Kuberasampath et al. |
| 2003/0236573 A1 | 12/2003 | Evans et al. |
| 2004/0002558 A1 | 1/2004 | McKay |
| 2004/0034434 A1 | 2/2004 | Evans et al. |
| 2004/0064193 A1 | 4/2004 | Evans et al. |
| 2004/0127987 A1 | 7/2004 | Evans et al. |
| 2004/0138758 A1 | 7/2004 | Evans et al. |
| 2005/0169895 A1 * | 8/2005 | Melvik et al. ................ 424/93.7 |
| 2005/0186240 A1 | 8/2005 | Ringeisen et al. |
| 2005/0196425 A1 * | 9/2005 | Zamora et al. ................ 424/426 |
| 2006/0002980 A1 * | 1/2006 | Ringeisen et al. ............ 424/426 |
| 2007/0178158 A1 * | 8/2007 | Knaack et al. ................ 424/484 |
| 2007/0190083 A1 * | 8/2007 | Scifert et al. ................. 424/400 |
| 2009/0010983 A1 * | 1/2009 | Melvik et al. ................ 424/422 |

* cited by examiner

COMPOSITIONS FOR TREATING BONE DEFECTS

BACKGROUND

The present invention relates generally to medical implant compositions, and in certain aspects to malleable medical implant materials, such as putties, useful as carrier materials and/or bone graft materials.

A variety of materials have been suggested for the treatment of bone defects. In addition to traditional bone grafting, a number of synthetic bone graft substitutes have been used or explored, including several putty materials. To conduct bone through-growth effectively, implant materials derive benefit from the presence of substantial scaffolding material. Such scaffolding material must be combined in a composition that handles effectively during and after implant and in the case of carriers for growth factors such as morphogenetic proteins, the overall composition benefits from an effective utilization of the protein to promote or induce tissue growth through the scaffolding material.

In view of the background in the area, there exist needs for improved putty materials which maintain the desired combination of malleability and cohesiveness as well as exhibit the ability to conduct bone growth based upon native signals at the implant site and/or to effectively administer an added signal molecule at the implant site. In certain aspects, the present invention is directed to these needs.

SUMMARY

In certain aspects, the present invention relates to malleable medical implant formulations that include a noncollagenous scaffolding material combined with a biocompatible liquid organic binder. Accordingly, in certain embodiments, the invention provides an osteoinductive composition comprising a malleable, mechanically entangled mass of elongate, compliant noncollagenous scaffolding elements. The composition comprises sulfated glycosaminoglycan molecules bound to the scaffolding elements and a liquid organic binder that coats the scaffolding elements, wherein the liquid organic binder has a viscosity and is present in an amount that is effective to increase the cohesivity of the mechanically entangled mass of scaffolding elements. An osteoconductive calcium-containing particulate material is incorporated in the mechanically entangled mass of scaffolding elements in certain beneficial embodiments. In advantageous forms, an osteoinductive protein can be included in the composition, and the sulfated glycosaminoglycan can exhibit the capacity to bind the osteoinductive protein. In accordance with certain embodiments, the elongate noncollagenous scaffolding elements are ribbons of material having a median width in the range of about 0.2 mm to about 3 mm, a median length in the range of about 5 mm to about 20 mm, and a median thickness in the range of about 0.02 mm to about 0.2 mm. Such a composition can be comprised about 60% to about 75% by weight of the liquid organic binder. Also, the osteoinductive protein can be a bone morphogenic protein, for instance incorporated at a level of about 0.6 milligrams per cubic centimeter (mg/cc) to about 2 mg/cc in the overall composition. The calcium-containing particles in the composition can have an average particle diameter in the range of about 0.1 millimeters (mm) to about 5 mm, and/or can be incorporated at a level of about 0.25 g/cc to about 0.35 g/cc in the overall composition. The composition can further include the scaffolding elements at a level of about 0.04 g/cc to about 0.1 g/cc. The viscosity of the liquid organic binder can range from about 1 centipoise to about 200 centipoises in certain embodiments. The osteoinductive composition is desirably a cohesive, shape-retaining putty.

In other embodiments, the invention provides osteoinductive compositions that comprise a malleable mechanically entangled mass of elongate, compliant scaffolding elements, wherein said scaffolding elements are composed of (i) one or more synthetic polymers, (ii) one or more plant-derived biopolymers, (iii) one or more insect-derived biopolymers, or (iv) mixtures of two or all of (i), (ii) and (iii). The compositions include a liquid organic binder coating the scaffolding elements, wherein the liquid organic binder has such a viscosity and is present in such an amount so as to be effective to increase the cohesivity of the mechanically entangled mass. An osteoinductive factor is incorporated in said mechanically entangled mass, and the scaffolding elements exhibit a capacity to bind the osteoinductive factor. In advantageous forms, an osteoinductive protein can be included in the composition, and a sulfated glycosaminoglycan can be incorporated in or on the scaffolding elements and exhibit the capacity to bind the osteoinductive protein. In accordance with certain embodiments, the elongate scaffolding elements are ribbons of material having a median width in the range of about 0.2 mm to about 3 mm, a median length in the range of about 5 mm to about 20 mm, and a median thickness in the range of about 0.02 mm to about 0.2 mm. Such a composition can be comprised about 60% to about 75% by weight of the liquid organic binder. Also, the osteoinductive protein can be a bone morphogenic protein, for instance incorporated at a level of about 0.6 milligrams per cubic centimeter (mg/cc) to about 2 mg/cc in the overall composition. The composition can include calcium-containing particles having an average particle diameter in the range of about 0.1 mm to about 5 mm, and/or can be incorporated at a level of about 0.25 g/cc to about 0.35 g/cc in the overall composition. The composition can further include the scaffolding elements at a level of about 0.04 g/cc to about 0.1 g/cc. The viscosity of the liquid organic binder can range from about 1 centipoise to about 200 centipoises in certain embodiments. The osteoinductive composition is desirably a cohesive, shape-retaining putty.

In other embodiments, provided are methods for preparing an osteoinductive material for inducing bone growth in a patient. The methods comprise providing an osteoinductive implant material comprising an osteoconductive scaffolding material incorporating an osteoinductive protein. In a sterile operating field, the exterior surfaces of the osteoinductive implant material are coated with a biodegradable barrier substance to form a coated implant material, wherein the biodegradable barrier substance is effective to delay release of the osteoinductive protein from the scaffolding material.

In other embodiments, provided are methods for inducing bone growth in a patient. The methods comprise providing an osteoconductive scaffolding material, and incorporating an osteoinductive protein into the osteoinductive scaffolding material to form an osteoinductive-protein-loaded scaffolding material. The method further includes coating exterior surfaces of the loaded scaffolding material with a biodegradable barrier substance to form a coated implant material, wherein the biodegradable barrier substance is effective to delay release of the osteoinductive protein from the scaffolding material. The coated implant material is implanted in a patient at a site at which bone growth is desired.

In another embodiment, provided is an osteoinductive material for implantation to induce bone growth in a patient. The osteoinductive material comprises an osteoinductive implant material including an osteoconductive scaffolding material incorporating an osteoinductive protein. A coating is positioned upon exterior surfaces of the osteoinductive implant material, the coating including a biodegradable barrier substance and being effective to delay release of the osteoinductive protein from the scaffolding material. In certain forms, the scaffolding material exhibits the capacity to bind the osteoinductive protein.

In still further embodiments, the present invention provides methods for treating patients that involve implanting in the patients at least one medical composition as described herein, and/or prepared as described herein.

Additional embodiments as well as features and advantages of the present invention will be apparent to those of ordinary skill in the art from the descriptions herein.

DETAILED DESCRIPTION

Figure 1:
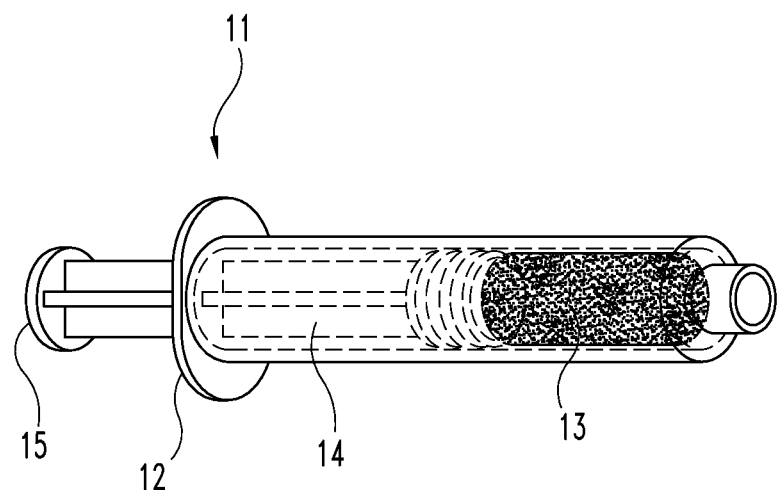
FIG. 1 provides a perspective view of a medical product of the invention including a medical paste or putty of the invention packaged within a terminally sterilized syringe device.

For the purposes of promoting an understanding of the principles of the invention, reference will now be made to certain embodiments and specific language will be used to describe the same. It will nevertheless be understood that no limitation of the scope of the invention is thereby intended, such alterations and further modifications in the illustrated device, and such further applications of the principles of the invention as described herein being contemplated as would normally occur to one skilled in the art to which the invention relates.

As disclosed above, in certain aspects, the present invention relates to malleable medical implant compositions, including for example putties, to methods and materials that are useful for preparing such compositions, and to uses of such compositions. Certain preferred medical compositions of the invention possess a combination of advantageous properties including high mineral content, malleability, cohesiveness, and shape retention. In this regard, as used herein the term "malleable" means that the material is capable of being permanently converted from a first shape to a second shape by the application of pressure. The term "cohesive" as used herein to describe a composition means that the composition tends to remain a singular, connected mass upon stretching, including the exhibition of the ability to elongate substantially without breaking upon stretching. In the context of stretching compositions of the invention containing insoluble bioresorbable ribbons, the advantageous compositions exhibit elongation, during which the existence of substantial levels of intermeshed ribbons clinging to one another becomes visually apparent. As used herein, the term "shape-retaining" as used to describe a composition means that the composition is highly viscous and unless acted upon with pressure tends to remain in the shape in which it is placed. This is contrasted to thinner paste form materials which readily flow, and thus would pool or puddle upon application to a surface in a range of temperatures from ambient room temperature (20° C.) to body temperature (37° C.). In certain features of the invention, novel combinations of ingredients provide a medical material that not only contains a significant, high level of large particulate calcium-containing particles, but also exhibits superior properties with respect to malleability, cohesiveness, and shape retention.

In certain embodiments, the solid phase of compositions of the invention contains elongate scaffolding elements such as fibers, ribbons or strands that are made from material that is noncollagenous and/or from a material composed of synthetic polymers, plant-derived biopolymers, insect-derived biopolymers, or mixtures of some or all thereof. In this regard, "noncollagenous" as used herein refers to materials that do not contain any collagen. Scaffolding materials can, for example, be prepared from one or more synthetic polymers. Such polymer(s) can be resorbable. Desirably, resorbable polymers are used and the elongate scaffolding elements will be resorbed within about 2 weeks to about 12 weeks after implantation of the composition in a patient, more desirably about four to about six weeks. Suitable resorbable synthetic polymers include, for instance, aliphatic polyesters, cellulose, copolymers of glycolide, copolymers of lactide, glycolide/l-lactide copolymers (PGA/PLLA), glycolide/trimethylene carbonate copolymers (PGA/TMC), hydrogel, lactide/tetramethylglycolide copolymers, lactide/trimethylene carbonate copolymers, lactide/[epsilon]-caprolactone copolymers, lactide/[sigma]-valerolactone copolymers, L-lactide/dl-lactide copolymers, methyl methacrylate-N-vinyl pyrrolidone copolymers, Nylon-2, PHBA/[gamma]-hydroxyvalerate copolymers (PHBA/HVA), PLA/polyethylene oxide copolymers, PLA-polyethylene oxide (PELA), poly (amino acids), poly(trimethylene carbonates), poly hydroxyalkanoate polymers (PHA), poly(alklyene oxalates), poly(butylene diglycolate), poly(hydroxy butyrate) (PHB), poly(n-vinyl pyrrolidone), poly(ortho esters), polyalkyl-2-cyanoacrylates, polyanhydrides, polycyanoacrylates, polydepsipeptides, polydihydropyrans, poly-dl-lactide (PDLLA), polyesteramides, polyesters of oxalic acid, polyglycolide (PGA), polyiminocarbonates, polylactides (PLA), poly-1-lactide (PLLA), polyorthoesters, poly-p-dioxanone (PDO), polypeptides, polyphosphazenes, polysaccharides, polyurethanes (PU), polyvinyl alcohol (PVA), poly-[beta]-hydroxypropionate (PHPA), poly-[beta]-hydroxybutyrate (PBA), poly-[sigma]-valerolactone, poly-[beta]-alkanoic acids, poly-[beta]-malic acid (PMLA), poly-[epsilon]-caprolactone (PCL), pseudo-poly(amino acids), trimethylene carbonate (TMC), tyrosine based polymers, and others.

Polyhydroxyalkanoate polymers that can be used include polyhydroxyalkanoate (PHA) polyesters such as polymers or copolymers of hydroxybutyrates, including 3-hydroxybutyrate and/or 4-hydroxybutyrate. Poly-3-hydroxybutyrate-co-4-hydroxybutyrate (a co-polymer of (R)-3-hydroxybutyrate and 4-hydroxybutyrate) can be used. Other useful copolymers in the PHA family include poly-3-hydroxybutyrate-c-o-3-hydroxyvalerate, poly-hydroxyoctanoate-co-hexanoate and poly-4-hydoxybutyrate-co-glycolate. Suitable methods for preparing the PHA polyesters are described in Williams, S. F. and Peoples, O. P. CHEMTECH, 26:38-44 (1996), Williams, S. F. and Peoples, O. P., Chem. Br., 33:29-32 (1997), U.S. Pat. No. 4,910,145 to Holmes, P. A. and Lim, G. B.; Byrom, D., Miscellaneous Biomaterials, in D. Byrom, Ed., Biomaterials MacMillan Publishers, London, 1991, pp. 333-359; Hocking, P. J. and Marchessault, R. H. Biopolyesters, G. J. L. Griffin, Ed., Chemistry and Technology of Biodegradable Polymers, Chapman and Hall, London, 1994, pp. 48-96; Holmes, P. A., Biologically Produced (R)-3-hydroxyalkanoate Polymers and Copolymers, in D. C. Bassett Ed., Developments in Crystalline Polymers, Elsevier, London, Vol. 2, 1988, pp. 1-65; Lafferty et al., Microbial Production of Poly-b-hydroxybutyric acid, H. J. Rehm and G. Reed, Eds., Biotechnology, Verlagsgesellschaft, Weinheim, Vol. 66, 1988, pp. 135-176; Muller and Seebach, Angew. Chem. Int. Ed. Engl. 32:477-502 (1993); Steinbuichel, A. Polyhydroxyalkanoic Acids, in D. Byrom Ed., Biomaterials, MacMillan Publishers, London, 1991, pp. 123-213; and, Williams and Peoples, CHEMTECH, 26:38-44, (1996); Steinbutchel and Wiese, Appl. Microbiol. Biotechnol., 37:691-697 (1992); U.S. Pat. Nos. 5,245,023; 5,250,430; 5,480,794; 5,512,669; 5,534,432; Agostini, D. E. et al., Polym. Sci., Part A-1, 9:2775-2787 (1971); Gross, R. A. et al., Macromolecules, 21:2657-2668 (1988); Dubois, P. I. et al., Macromolecules, 26:4407-4412 (1993); Le Borgne, A. and Spassky, N., Polymer, 30:2312-2319 (1989); Tanahashi, N. and Doi, Y., Macromolecules, 24:5732-5733 (1991); Hori, Y. M. et al., Macromolecules, 26:4388-4390 (1993); Kemnitzer, J. E. et al., Macromolecules, 26:1221-1229 (1993); Hori, Y. M. et al., Macromolecules, 26:5533-5534 (1993); Hocking, P. J. and Marchessault, R. H., Polym. Bull., 30:163-170 (1993); Xie, W. et al., Macromolecules, 30:6997-6998 (1997), U.S. Pat. No. 5,563,239 to Hubbs, J. C. and Harrison, M. N., and Braunegg, G. et al., J. Biotechnol. 65:127-161 (1998). Suitable PHA polymers can also be obtained commercially from Tepha, Inc. (Cambridge, Mass.) under the trade designations PHA4400 (poly-4-hydroxybutyrate), PHA 3444 (poly-3-hydroxybutyrate-co-4-hydroxybutyrate), and PHA4422. (poly-4-hydoxybutyrate-co-glycolate).

Resorbable insect-derived biopolymers such as resorbable silk materials, for example as available from Serica Technologies, Inc., and/or hyaluronic acid, can also be used to prepare the elongate scaffolding element materials used herein. Additionally, resorbable plant-derived materials can be used in the preparation of the elongate scaffolding elements. Plant-derived materials can include for example polysaccharides such as alginates and others identified herein, which can be processed to form solid materials by processes including crosslinking and/or other techniques. Methods useful for preparing or isolating such polymers or other materials and for forming elongate strands or other similar scaffolding structures are known in the art and can be used in accordance with the present invention.

The elongate scaffolding elements can constitute about 2% to about 50% by weight (dry) of the overall composition, more desirably about 10% to about 50%. It will be understood however that other levels can be used within other aspects of the invention.

In preferred forms, the elongate scaffolding elements will be in the form of ribbons having a median width of at least about 0.2 mm, and in certain forms at least about 0.5 mm. In certain embodiments, the ribbons have a median width in the range of about 0.2 mm to about 3 mm (more preferably about 0.5 mm to about 3 mm), a median length in the range of about 5 mm to about 20 mm, and a median thickness in the range of about 0.02 mm to about 0.2 mm. Such ribbon-form elements can cooperate in the composition to provide an effective scaffold for cellular invasion and penetration through the implanted volume of composition.

In some embodiments, the elongate scaffolding elements will be modified to modulate their interaction with one or more morphogenic proteins or other osteoinductive factors. For example, the scaffolding elements can be modified to provide or enhance their ability to bind to an osteoinductive protein and/or other factor. Illustratively, the scaffolding elements can incorporate and/or be attached to one or more substances that promote retention of one or more osteoinductive factors, such as but not limited to morphogenic proteins, in or on the elements. Illustratively, the elongate scaffolding elements can incorporate or be attached to sulfated glycosaminoglycan molecules to which the osteoinductive factor binds. Suitable such sulfated glycosaminoglycans include for instance heparin and/or dextran sulfate. The osteoinductive factor-binding materials may be incorporated into the scaffolding elements upon their formation and/or pre-formed scaffolding elements can be attached to (e.g. coated with) the osteoinductive-factor-binding materials. In one mode, heparin or other similar sulfated glycosaminoglycans can be attached to the surface of the scaffolding elements by a technique involving end point bonding, e.g. as described in connection with the Carmeda Bioactive Surface (CBAS) technique in which heparin is modified to form an aldehydes group at one end of the molecule, and the aldehyde groups are reacted with the material to be coated with heparin to form an end-point-attachment. Other covalent or non-covalent modes of bonding the heparin or other osteoinductive factor-binding ligands to the scaffolding element material or its precursor include, for example, ionic bonding, complexation, covalent crosslinking (e.g. using glutaraldehyde as a coupling agent), thermofixation, and coupling agents such as aminosilane coupling agents. Additionally or alternatively, the surfaces of the scaffolding elements can be treated to modify their charge, for example adding or enhancing a negative or positive surface charge, in such a fashion as to increase the ability of the scaffolding elements to bind to a given osteogenic protein or other factor.

The elongate scaffolding elements can be treated to apply the heparin or other osteoinductive factor-binding coating, and/or the heparin or other binding substance may be incorporated within or coated on a precursor material that is subsequently processed to form the scaffolding elements, e.g. by cutting or grinding a precursor solid material, spinning (e.g. melt spinning or electrospinning) or other techniques suitable for forming scaffolding elements of the modified bioresorbable material.

Heparin or another sulfated glycosaminoglycan that is permanently or releasably bound to the scaffolding elements, and/or other amounts of heparin or sulfated glycosaminoglycans present in the composition (e.g. an amount dissolved or suspended in the liquid organic binder), can also serve to enhance osteoblast differentiation induced by BMPs by protecting them from degradation and by inhibiting BMP antagonists such as NOGGIN. The protected BMP can for example be one that is introduced with the composition and/or one that is natively produced in the patient receiving the implanted composition.

Malleable compositions of the invention also include a biocompatible liquid organic binder. In this regard, the term "organic" used in this context means that the liquid binder is or contains at least one carbon-containing compound. The liquid organic binder can be an aqueous medium or a non-aqueous medium, and in certain embodiments exhibits a viscosity in the range of 1 centipoise (cps) to 200 cps. The liquid organic binder can be or comprise one or more of carboxymethylcellulose, glycerin, a polysaccharide such as alginate, or chitosan. In certain aspects, the liquid organic binder will be an aqueous medium comprising a biocompatible organic substance that is soluble in the medium and increases the viscosity of the medium. In such embodiments, or other embodiments, the liquid organic binder can comprise an amount of a polysaccharide compound. In addition, the polysaccharide-containing liquid organic binder, when used, can serve to plasticize the solids in the composition so as to improve the flow properties and/or reduce the tackiness of the overall malleable composition.

Polysaccharides that can be used as thickeners in the liquid organic binder include, for example, alginate, hyaluronic acid, chondroitin sulfate, dextran, dextran sulfate, heparin, heparin sulfate, chitosan, gellan gum, xanthan gum, guar gum, and K-carrageenan, or mixtures of two or more of these or other polysaccharides.

Medical grade polysaccharides suitable for use in aspects of the invention can be prepared using known techniques or purchased from commercial sources. Illustratively, purification techniques for preparing medical grade polysaccharides may include conventional separation techniques such as chromatography, membrane filtration, precipitation, extraction, or other suitable techniques. Medical grade sodium alginate may be commercially obtained, for example, from Medipol SA (Lausanne, Switzerland), or from NovaMatrix FMC Biopolymer (Philadelphia, Pa., Ultrapure PRONOVA brand (endotoxin level <100 endotoxin units per gram)).

Alginate polymers contain large variations in the total content of M and G, and the relative content of sequence structures also varies largely (G-blocks, M-blocks and MG alternating sequences) as well as the length of the sequences along the polymer chain. In some embodiments, one or more alginate polymers of the malleable composition can contain more than 50% alpha-L-guluronic acid. In some embodiments, one or more alginate polymers of the composition can contain more than 60% alpha-L-guluronic acid. In some embodiments, one or more alginate polymers of the composition can contain 60% to 80% alpha-L-guluronic acid.

In certain embodiments, alginate polymers used in compositions as described herein may have average molecular weights ranging from 2 to 1000 kilodaltons (kD). The molecular weight of alginates can affect the properties of the malleable composition. Generally, lower molecular weight alginates will be more biodegradable. In some embodiments, the alginate polymers have an average molecule weight of from 5 to 350 kD. In some embodiments, the alginate polymers have an average molecule weight of from 2 to 100 kD. In some embodiments, the alginate polymers have an average molecule weight of from 50 to 500 kD. In some embodiments, the alginate polymers have an average molecule weight of from 100 to 1000 kD. The molecular weights identified in this paragraph can similarly apply to other polysaccharides when used in the invention. The alginate, when used, may possess a viscosity in a 1% solution measured at 20 degrees centigrade of from 25 to 1000 mPas and in some embodiments, 50 to 1000 mPas (1% solution, 20° C.), and/or may be used in a 2% to 20% by weight aqueous solution.

In certain embodiments, the liquid organic binder contains an ionic polysaccharide that is capable of forming a thermally irreversible ionically-crosslinked gel upon combination with monovalent, divalent or other polyvalent ionic species, in many cases a cationic species. Ionically crosslinkable materials contemplated for use in the practice of the present invention include ionic materials such as alginates, chitosan, gellan gum, xanthan gum, hyaluronic acid, heparin, pectin, carrageenan, and the like. Many suitable polysaccharides are plant-derived polysaccharides, such as alginates and pectins (including gel-forming derivatives thereof). Other suitable polysaccharides can be derived from bacteria, including for example gellan gums.

Aqueous solutions of ionic polysaccharides can generally form ionically-crosslinked gels upon contact with aqueous solutions of counter-ions. For instance, useful agents for ionically crosslinking alginate, pectin and other similar polysaccharides include cationic gelling agents, preferably including divalent or trivalent cations. Useful divalent cations for these purposes include the alkaline earth metals, especially calcium and strontium. Aluminum is a useful crosslinking trivalent cation. These ionic crosslinking agents will usually be provided by salts. Useful anionic counter-ions for the calcium or other salts are desirably selected from pharmaceutically-acceptable anions such as chlorides, gluconates, fluorides, citrates, phosphates, tartrates, sulphates, acetates, borates, and the like. An especially preferred ionic crosslinking agent for use with an alginate or pectin compound is provided by calcium chloride. The ionic polysaccharide chitosan can also be used, and can be ionically crosslinked with multivalent, anionic gelling agents. Such agents include metal polyphosphates, such as an alkali metal or ammonium polyphosphate, pyrophosphates or metaphosphates. Citrates can also be used. These anionic crosslinking agents will also usually be provided by salts. The cationic counter-ion for the polyphosphate or other salt can be any suitable, biocompatible or pharmaceutically-acceptable cation including for instance sodium, potassium, or ammonium. Additionally, polysaccharides which gel by exposure to monovalent cations, including bacterial polysaccharides, such as gellan gum, and plant polysaccharides, such as carrageenans, may be crosslinked to form a hydrogel using methods analogous to those available for the crosslinking of alginates described above. Polysaccharides which gel in the presence of monovalent cations, such as gellan gums, can also be used. Such polysaccharides may form gels upon exposure, for example, to a solution comprising physiological levels of sodium. Many other biocompatible polysaccharides, including plant-derived and animal-derived materials, as well as corresponding ionic crosslinking agents, are known and can also be used in aspects of the present invention.

When ionic polysaccharides that are capable of forming thermally-irreversible ionically-crosslinked gels are used in the liquid organic binder, it will be understood that in malleable compositions of the present invention these polysaccharides will be ionically crosslinked, if at all, only to an extent that does not eliminate the malleable nature of the implant material. Thus, within aspects of the present invention, no or substantially no ionic crosslinking agent will be added, or in some cases only a relatively small amount of ionic crosslinking agent can be added in order to increase the viscosity of the overall formulation. On the other hand, in other aspects of the invention, malleable compositions as described herein can be contacted with an amount of a liquid medium containing an ionic crosslinking agent immediately prior to, during, or after implantation of the material into a patient. Illustratively, a malleable composition as described herein can be co-administered with a liquid medium of ionic crosslinker, as in the case of a dual-barrel syringe administration by which the malleable composition and crosslinker are admixed as they exit the syringe. Alternatively, a previously-implanted amount of the malleable composition can be washed with a solution or other liquid medium containing an appropriate ionic crosslinking agent to stiffen the implanted material in situ.

In certain embodiments, compositions of the invention include the insoluble elongate scaffolding elements at a level of 0.04 g/cc to 0.1 g/cc of the composition, and/or include a polysaccharide (e.g. in the liquid organic binder) at a level of 0.01 g/cc to 0.08 g/cc of the composition. In other embodiments, such compositions include the insoluble bioresorbable scaffolding elements at a level of about 0.05 to 0.08 g/cc in the composition. When one or more polysaccharides are used in an aqueous binder, advantageous compositions can include the insoluble elongate scaffolding elements in an amount (percent by weight) that is at least equal to or greater than the total amount of polysaccharide(s), to contribute beneficially to the desired handling and implant properties of the compositions, e.g. in the provision of a shape-retaining putty material.

In certain forms, medical putties or other compositions of the present invention also include an amount of a particulate calcium-containing material. In certain aspects of the invention, such a particulate material is incorporated in the inventive composition at a level of at least about 0.25 g/cc of composition, and typically in the range of about 0.25 g/cc to about 0.35 g/cc. Such relatively high levels of calcium-containing particles can be helpful in providing additional scaffold material for the ingrowth of new bone.

The calcium-containing particulate material used in the present invention can include a natural or synthetic mineral or mixture of mineral materials that is effective to provide a scaffold for bone ingrowth. Illustratively, a mineral matrix may be selected from one or more materials from the group consisting of bone particles, Bioglass®, tricalcium phosphate, biphasic calcium phosphate, hydroxyapatite, corraline hydroxyapatite, and biocompatible ceramics. Biphasic calcium phosphate is a particularly desirable synthetic ceramic for use in the invention. Such biphasic calcium phosphate can have a tricalcium phosphate:hydroxyapatite weight ratio of about 50:50 to about 95:5, more preferably about 70:30 to about 95:5, even more preferably about 80:20 to about 90:10, and most preferably about 85:15. The calcium-containing particulate material can have an average particle diameter between about 0.1 and 5 mm, more typically between about 0.1 and 2 mm.

In certain embodiments, the calcium-containing particulate incorporated into the inventive composition can include a substantial component of relatively larger particles in combination with relatively smaller particles. In certain aspects, the calcium-containing particulate can be constituted at least 10 weight % by particles having a maximum dimension of greater than about 2 mm, or greater than about 3 mm (e.g. in the range of about 3 mm to about 5 mm) and at least 10 weight % by particles having a maximum dimension of less than about 1 mm. In further aspects, the calcium-containing particulate can be constituted at least 20 weight % by particles having a maximum dimension of greater than about 2 mm, or greater than about 3 mm (e.g. in the range of about 3 mm to about 5 mm) and at least 20 weight % by particles having a maximum dimension of less than about 1 mm. In still further embodiments, the calcium-containing particulate can be constituted about 10 weight % to about 40 weight % by particles having a maximum dimension of greater than about 2 mm, or greater than about 3 mm (e.g. in the range of about 3 mm to about 5 mm) and about 90 weight % to about 60 weight % by particles having a maximum dimension of less than about 1 mm. It will be understood that particles as described above may have the given dimensions along one axis or along two or three axes. Products having such calcium-containing particle sizes can be prepared, for example, by blending separate particulate products having the respective particle size distributions. The presence of relatively large calcium-containing particles in combination with smaller particles can provide an overall composition that resists compression upon impingement by soft tissues at an implant site, and that also can exhibit beneficial handling and implant properties.

In certain embodiments, the calcium-containing particulate material constitutes about 50% to about 98% by weight (dry) of the overall composition, more desirably about 70% to about 90%. It will be understood however that other levels of such particulate material can be used in other aspects of the invention.

Malleable compositions of the invention can include a significant proportion of the liquid organic binder, for instance with the liquid organic binder constituting about 50% or more by weight of the overall composition. In one aspect, a malleable, cohesive, shape-retaining composition of the invention comprises about 60% to about 75% by weight of the liquid organic binder material. It will be understood however that higher or lower levels of the liquid binder can also be used to prepare either firmer (e.g. dampened solid matrices) or more flowable materials, such as pastes, for implantation in a patient. As will also be appreciated by those skilled in the art, in many instances, the pH, ionic strength, and/or other similar characteristics of the liquid binder can be selected to control its viscosity. Illustratively, these and other parameters of the liquid binder component can be controlled to prevent undesired levels of ionic crosslinking of any polysaccharide(s) present that would unduly disrupt the malleable character of a preferred implant composition.

In certain embodiments, the osteoinductive substance can include one or more growth factors that is/are effective in inducing formation of bone. Desirably, the growth factor will be from a class of proteins known generally as bone morphogenic proteins (BMPs), and can in certain embodiments be recombinant human (rh) BMPs. These BMP proteins, which are known to have osteogenic, chondrogenic and other growth and differentiation activities, include rhBMP-2, rhBMP-3, rhBMP4 (also referred to as rhBMP-2B), rhBMP-5, rhBMP-6, rhBMP-7 (rhOP-1), rhBMP-8, rhBMP-9, rhBMP-12, rhBMP-13, rhBMP-15, rhBMP-16, rhBMP-17, rhBMP-18, rhGDF-1, rhGDF-3, rhGDF-5, rhGDF-6, rhGDF-7, rhGDF-8, rhGDF-9, rhGDF-10, rhGDF-11, rhGDF-12, rhGDF-14. For example, BMP-2, BMP-3, fBMP-4, BMP-5, BMP-6 and BMP-7, disclosed in U.S. Pat. Nos. 5,108,922; 5,013,649; 5,116,738; 5,106,748; 5,187,076; and 5,141,905; BMP-8, disclosed in PCT publication WO91/18098; and BMP-9, disclosed in PCT publication WO93/00432, BMP-10, disclosed in U.S. Pat. No. 5,637,480; BMP-11, disclosed in U.S. Pat. No. 5,639,638, or BMP-12 or BMP-13, disclosed in U.S. Pat. No. 5,658,882, BMP-15, disclosed U.S. Pat. No. 5,635,372 and BMP-16, disclosed in U.S. Pat. Nos. 5,965,403 and 6,331,612. Other compositions which may also be useful include Vgr-2, and any of the growth and differentiation factors including those described in PCT applications WO94/15965; WO94/15949; WO95/01801; WO95/01802; WO94/21681; WO94/15966; WO95/10539; WO96/01845; WO96/02559 and others. Also useful in the present invention may be BIP, disclosed in WO94/01557; HP00269, disclosed in JP Publication number: 7-250688; and MP52, disclosed in PCT application WO93/16099. The growth factor may also be a LIM Mineralization Protein (LMP), including for example one or more of those disclosed in U.S. Pat. Nos. 6,858,431 and 7,045,614. The disclosures of all of these Patents and applications are hereby incorporated herein by reference. Also useful in the present invention are heterodimers of the above and modified proteins or partial deletion products (biologically active fragments) thereof. These proteins can be used individually or in mixtures of two or more. rhBMP-2 or biologically active derivatives or fragments thereof that exhibit an ability to induce bone growth are preferred.

The BMP or other osteoinductive protein may be recombinantly produced. The BMP may be homodimeric, or may be heterodimeric with other BMPs (e.g., a heterodimer composed of one monomer each of BMP-2 and BMP-6) or with other members of the TGF-beta superfamily, such as activins, inhibins and TGF-beta 1 (e.g., a heterodimer composed of one monomer each of a BMP and a related member of the TGF-beta superfamily). Examples of such heterodimeric proteins are described for example in Published PCT Patent Application WO 93/09229, the specification of which is hereby incorporated herein by reference. The amount of osteogenic protein useful herein is that amount effective to stimulate increased osteogenic activity of infiltrating progenitor cells, and will depend upon several factors including the size, location, and nature of the defect being treated, and the carrier and particular protein being employed. In certain embodiments, the amount of osteogenic protein to be delivered to the implant site will be in a range of from about 0.05 to about 1.5 mg.

Compositions described herein can include a bone morphogenic protein or another osteoinductive factor incorporated therein in an effective amount to render the composition osteoinductive when implanted in a mammal, such as a human patient. In one embodiment, an inventive composition includes a bone morphogenic protein or other osteogenic protein at a level of about 0.6 milligrams per cubic centimeter (mg/cc) of putty to about 2 mg/cc of putty, advantageously at a level of about 0.8 mg/cc to about 1.8 mg/cc.

Other therapeutic growth factors or substances may also be used in putties or other compositions of the present invention, especially those that can be used to stimulate bone formation. Such proteins are known and include, for example, demineralized bone matrix, platelet-derived growth factors, insulin-like growth factors, cartilage-derived morphogenic proteins, statins, and transforming growth factors, including TGF-$\alpha$ and TGF-$\beta$.

The osteoinductive proteins and/or other biologically active agents to be used in the present invention can be provided in liquid formulations, for example buffered aqueous formulations. In certain embodiments, such formulations are mixed with, received upon and/or within, or otherwise combined with a dried implant material which is then manipulated to prepare a malleable osteoinductive material of the invention.

As further enhancements of the compositions of the present invention, those skilled in the art will readily appreciate that other biologically active agents can be incorporated into the compositions. Such additional agents include, but are not limited to, microglobulin-beta, antibiotics, antifungal agents, wetting agents, steroids and non-steroidal anti-inflammatory compounds.

In another aspect, the present invention provides a dry implant material that can be combined with an appropriate amount of a liquid medium in order to prepare a malleable implant material as described herein. The dry implant material can be in any suitable form, including for example a mixed powder. In advantageous forms, the dry implant material will be a porous body that includes the bioresorbable scaffolding element material. The body can also include a particulate calcium-containing material as described herein embedded within the disruptable matrix. The dried, porous implant body or other dry material can be comprised about 70% to about 90% by weight of the particulate calcium-containing material and about 10% to about 30% by weight of the scaffolding element material. When a water-soluble organic compound, for example a polysaccharide, is to be incorporated in a liquid organic binder, it can also be incorporated in the dried porous body or other material, e.g. in an amount of about 1% to about 15% by weight. In certain embodiments, the dried, porous implant body or other material can include a polysaccharide in an amount from about 6% to about 10% by weight. In alternative embodiments that ultimately use a polysaccharide(s) or other organic substances in the liquid organic binder, the dried material can be free of the polysaccharide or other organic substance, but the wetting medium applied to dried material can include the polysaccharide or other organic substance. Combinations of these features are also contemplated herein, e.g. wherein one or more polysaccharides or other binder-forming organic substances, are included in each of the wetting medium and the dried material. The organic binder-forming substances in the wetting medium and dried material can also be the same as, or different from, each other. These and other alternatives will be apparent to those of ordinary skill in the art from the descriptions herein.

In certain embodiments, a dried, porous body as discussed above can have a density of between about 0.1 g/cc to about 0.3 g/cc, more desirably between about 0.15 g/cc and about 0.25 g/cc. Such dried, porous implant bodies can also exhibit porosities of at least about 50%, more desirably at least about 70% up to about 90%, and in certain embodiments in the range of about 80% to about 90%.

Dried, porous implant bodies in accordance with the invention can be provided in any suitable shape, including cylinders, cubes, chunks, pellets or other shapes. In certain aspects, the dried, porous implant body can define a reservoir for receiving amounts of a wetting liquid, e.g. to be used in the preparation of a putty or other malleable material from the dried implant material or used simply to wet the body for implant.

The dried porous body can be prepared using any suitable technique, including for example casting a liquid medium containing the dry ingredients, and then drying that medium by any appropriate means such as air drying or lyophilization. In this regard, the concentration of solids and other material in the liquid medium can be adjusted to control the ultimate porosity of the dried material, with lower solids concentrations typically providing higher porosities, and higher solids concentrations typically providing lower porosities. Additional variation of the porosity may be imparted by modifying the drying technique, including for example my modifying the lyophilization cycle to avoid substantial collapse or contraction of the cast material during drying. These and other porosity control parameters may be manipulated to control the porosity of the formed body.

Compositions of the present invention can be manufactured in a ready-to-use format and packaged in a medically acceptable container for wetted malleable materials. In some embodiments, as illustrated in FIG. 1, the ready-to-use medical product can be a product 11 including a syringe device 12 containing an amount of a malleable composition 13 of the invention. The composition is contained within syringe barrel 14, and is transferable from the barrel 14 by actuating a plunger 15.

Figure 2:
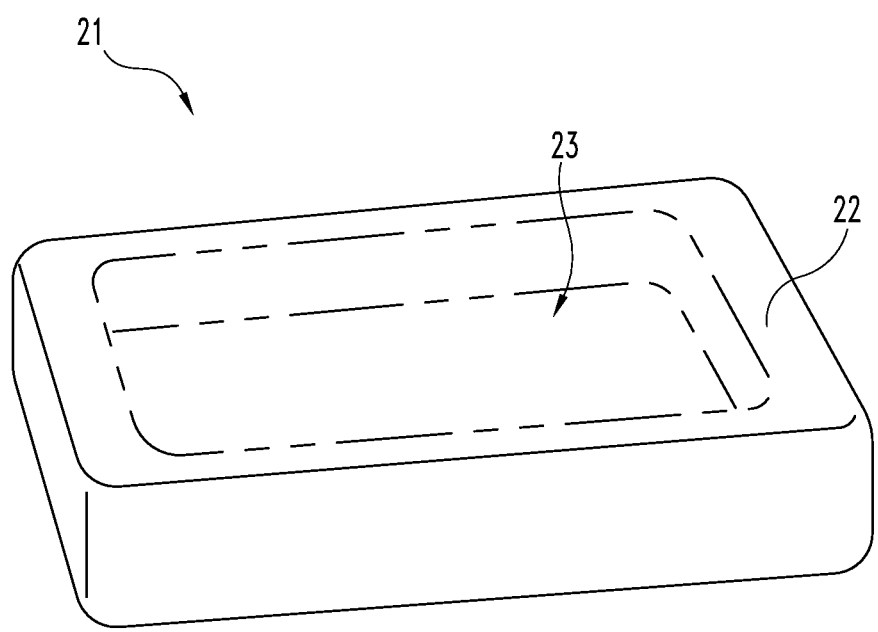
FIG. 2 provides a perspective view of a dry disruptable body that can be used to prepare malleable implant compositions of the invention.

Compositions of the invention can also be prepared on-site, at or near the time of surgery. For instance, dry materials can be provided in the appropriate amounts in a dried porous body as discussed above, and a suitable liquid such as a buffered aqueous solution or a liquid organic binder as described above can be combined with the dry materials and mixed to form malleable implant compositions. With reference to FIG. 2, in one form, an inventive product 21 includes a body 22 of dry materials including at least the elongate scaffolding material (e.g. including bound heparin or other sulfated glycosaminoglycans) and a calcium-containing particulate material is provided. The body 22 of dry materials may also include an organic binder material (e.g. one or more polysaccharides) and/or an osteogenic factor. Body 22 can optionally define a reservoir 23 for receiving and retaining amounts of the liquid medium to be combined with the dry materials as it soaks into the body 22. The body 22 can thereafter be disrupted, e.g. by manual kneading, mixing or otherwise, to form a malleable composition of the invention.

Typically, the combination of a disruptable, dried porous implant body of the invention with a liquid, and the physical kneading or other mixing of the resultant mass, will result in a reduction of the volume of the dried porous body, for example resulting in a malleable composition volume that is about 30% to about 70% of that of the original implant body, more typically about 40% to about 60%. This is a result of a breakdown of the original porosity of the dried implant body to form a relatively less porous or non-porous malleable implant composition. The liquid can be an aqueous substance, including for instance sterile water, physiological saline or other solutions (with or without organic co-solvents), emulsions or suspensions that provide adequate wetting characteristics to form malleable compositions of the invention.

In use, the implant compositions of the invention can be implanted at a site at which bone growth is desired, e.g. to treat a disease, defect or location of trauma, and/or to promote artificial arthrodesis. The malleable form of certain inventive compositions enables their positioning, shaping and/or molding within voids, defects or other areas in which new bone growth is desired. In particularly advantageous embodiments, the malleable composition will be in the form of a shape-retaining putty material that provides sufficient three-dimensional integrity to resist substantial compression when impinged by adjacent soft tissues of the body at a bony implant site.

In certain embodiments, all insoluble solids in compositions of the invention will be free from collagen. In other embodiments, the entire compositions of the invention will be free from collagen. In further embodiments, the insoluble solids in compositions of the invention will be free or essentially free from any mammalian-derived protein, or alternatively free or essentially free from any animal-derived protein. In still further embodiments, the entire compositions of the invention will be free or essentially free from mammalian-derived protein, or alternatively free or essentially free from any animal-derived protein. The term "essentially free from" as used in this context excludes the presence of the identified substance (e.g. collagen or protein material) other than that which might occur as a trace impurity, e.g. in the preparation of other materials (e.g. non-collagen materials or non-protein materials) derived from mammalian or other animal tissue.

Bone repair sites that can be treated with compositions of the invention include, for instance, those resulting from injury, defects brought about during the course of surgery, infection, malignancy or developmental malformation. The compositions can be used in a wide variety of orthopedic, periodontal, neurosurgical and oral and maxillofacial surgical procedures including, but not limited to: the repair of simple and compound fractures and non-unions; external and internal fixations; joint reconstructions such as arthrodesis; general arthroplasty; cup arthroplasty of the hip; femoral and humeral head replacement; femoral head surface replacement and total joint replacement; repairs of the vertebral column including spinal fusion and internal fixation; tumor surgery, e.g., deficit filing; discectomy; laminectomy; excision of spinal cord tumors; anterior cervical and thoracic operations; repairs of spinal injuries; scoliosis, lordosis and kyphosis treatments; intermaxillary fixation of fractures; mentoplasty; temporomandibular joint replacement; alveolar ridge augmentation and reconstruction; inlay osteoimplants; implant placement and revision; sinus lifts; cosmetic enhancement; etc. Specific bones which can be repaired or replaced with the compositions include, but are not limited to: the ethmoid; frontal; nasal; occipital; parietal; temporal; mandible; maxilla; zygomatic; cervical vertebra; thoracic vertebra; lumbar vertebra; sacrum; rib; sternum; clavicle; scapula; humerus; radius; ulna; carpal bones; metacarpal bones; phalanges; ilium; ischium; pubis; femur; tibia; fibula; patella; calcaneus; tarsal and metatarsal bones.

Where a composition of the invention is osteoinductive, once in place, it can effectively induce the ingrowth of bone into the desired area even in a human or other primate subject such as a human exhibiting a relatively slow rate of bone formation compared to smaller mammals, for example rodents or rabbits.

Compositions of the invention are especially advantageous when used in bones or bone portions that are vascularized to only moderate or low levels. These areas present particularly low rates of bone formation, and as such the rapid resorption of the carrier poses enhanced difficulties. Examples of moderate or only slightly vascularized sites include, for example, transverse processes or other posterior elements of the spine, the diaphysis of long bones, in particular the mid diaphysis of the tibia, and cranial defects. An especially preferred use of compositions of the invention is as an implant to promote arthrodesis between vertebrae in spinal fusions in humans or other mammals, including for example interbody, posterior and/or posterolateral fusion techniques.

In addition, in accordance with other aspects of the invention, the compositions of the invention can be incorporated in, on or around a load-bearing spinal or other orthopedic implant device (e.g. having a compressive strength of at least about 10000 N) such as a fusion cage, dowel, or other device having a pocket, chamber or other cavity for containing an osteoinductive and/or osteoconductive composition, and used in a spinal fusion such as an interbody fusion. In one illustrative example, an inventive composition can be used in conjunction with a load-bearing interbody spinal spacer to achieve an interbody fusion.

In some embodiments, medical compositions of the present invention can be used in combination with cells, including for instance progenitor and/or stem cells derived from embryonic or adult tissue sources and/or taken from culture. Illustratively, compositions of the invention can incorporate cells derived from blood, bone marrow, or other tissue sources from the patient to be treated (autologous cells) or from a suitable allogenic or xenogenic donor source. In certain embodiments of the invention, putties of the invention incorporate an enriched bone marrow fraction, prepared for example as described in US Patent Publication No. 2005/0130301 to McKay et al. published Jun. 16, 2005, publishing U.S. patent application Ser. No. 10/887,275 filed Jul. 8, 2004, which is hereby incorporated herein by reference in its entirety. Thus, the implant materials can incorporate a bone marrow fraction enriched in connective tissue growth components, that is prepared by centrifuging a biological sample (e.g. from the patient to be treated) to separate the sample into fractions including a fraction rich in connective tissue growth components. The fraction rich in connective tissue growth components can then be isolated from the separated sample, and incorporated into the putty material of the present invention, e.g. by using the fraction in or as the wetting medium for the dried, porous body as discussed hereinabove.

The present invention also provides medical kits that can be used to prepare implant compositions. Such kits can include a dried material (e.g. a dried porous body) as described herein, along with a liquid (e.g. aqueous) medium for combination with the body to form malleable implant composition or another wetted implant form, and/or another kit item such as a load-bearing implant (e.g. a spinal spacer) and/or an osteoinductive substance such as a BMP. In one specific form, such a medical kit will include the dried, porous body, a BMP in lyophilized form (e.g. rhBMP-2), and an aqueous medium for reconstitution of the BMP to prepare an aqueous formulation that can then be combined with the dried, porous body to prepare an osteoinductive putty or other wetted implant form of the invention.

In certain aspects of the invention, the liquid organic binder material, or another suitable biocompatible material, may be used as a barrier material in such a manner as to function as a physical barrier to delay the release of an osteogenic factor, such as an osteogenic protein, from the scaffolding material. In this regard, the osteogenic protein or other active factor can first be incorporated into or onto the scaffolding material, and the scaffolding material can then be coated with the barrier material sufficiently to delay the release of the protein or other factor from the scaffolding material. In preferred embodiment, the scaffolding material is transferred to the sterile patient operating field, and the barrier material is applied in the sterile operating field. Thus, in certain forms, a scaffolding material such as that described herein can be removed from a sterile package in the sterile operating field, and the medical care provider can then apply the barrier material as a coating upon the scaffolding material while in the operating field. The osteogenic protein or other factor can also be applied to the scaffolding material while in the sterile operating field, for example prior to the application of the barrier material. Alternatively or in addition, the osteogenic protein or other factor can be applied to the scaffolding material prior to entry into the sterile operating field, for example during product manufacture (e.g. as in the case where the sterile package contains the scaffolding material with a pre-applied amount of the osteogenic protein or other factor). In some modes of practice, the scaffolding material may exhibit the capacity to bind the osteogenic protein or other factor, e.g. by itself or with the addition of another material such as a sulfated glycosaminoglycan as described herein. In this manner, both a binding of the protein or other factor to the scaffolding material and the physical barrier material can beneficially delay release of the protein or other factor from the scaffolding material. This delay in release can beneficially maintain the protein or other factor within the implanted volume of scaffolding material for a longer period of time, thus providing an improved generation of bone through the implanted volume of scaffolding material. This delay in release can also be beneficial in generating bone formation through the implanted volume with less protein as compared with an equivalent scaffold without delayed release of protein.

The applied barrier material as discussed above can be a bioabsorbable substance. In this fashion, the barrier material can function as a temporary barrier to the release of the osteogenic factor, and thereafter become absorbed by the body of the patient. The barrier material can be selected and applied such that it is absorbed within a relatively short period of time after implant, for example within about two weeks. In certain forms, the barrier material will be substantially absorbed within about three to about seven days. In this fashion, the barrier material can promote early retention of the osteoinductive factor at the implant site during a period soon after implant in which native healing responses flush the implant site with bodily fluids and in which a native blood clot is formed in and around the implant region. After formation of the clot, the barrier material will have served its function of resisting early wash-out of the osteoinductive factor from the implanted composition and can be absorbed by the body soon thereafter.

In malleable compositions such as those described hereinabove, the barrier material can also serve as a binder, and can be incorporated substantially homogenously throughout the composition. In other embodiments, a coating or layer of barrier material can be selectively applied to an external surface of a volume of an implant composition such that it is non-homogenously incorporated in the overall implant material. In such embodiments, the volume of implant composition that is coated with barrier material can comprise a malleable composition and/or a three-dimensionally stable composition such as a sponge or other porous matrix. The implant composition can be loaded with the osteogenic factor (e.g. in the sterile field or during manufacture) and then externally coated with the barrier material prior to implantation within the patient.

The invention will now be more particularly described with reference to the following specific Examples. It will be understood that these Examples are illustrative and not limiting of the invention.

EXAMPLE 1

Preparation of Dried Implant Body

Sodium alginate is added with mixing to a preparation containing noncollagenous fibers (e.g. selected from among those listed below) adjusted with NaOH to have a pH in the range of 6.5-7.0. To this mixture are added biphasic calcium phosphate ceramic granules, with mixing. A dried, porous body is prepared by casting the resulting mixture into a cylindrical form and then lyophilizing the cast mixture. The relative amounts of the constituents of the dried body are as follows:

| Material | Wt % Solids |
|---|---|
| Biphasic CaP Granules* | 75% |
| Insoluble Noncollagenous Fibers (resorbable silk, poly-3-hydroxybutyrate-co-4-hydroxybutyrate, or other materials identified herein) | 15% |
| Sodium Alginate | 10% |

*Mastergraft ® Ceramic Granules, biphasic calcium phosphate granules containing 85% tricalcium phosphate and 15% hydroxyapatite, particle size 0.5-1.6 mm.

EXAMPLE 2

Preparation of Osteoconductive Putty

Phosphate buffered saline (PBS) is added to the body of Example 1, and the body is disrupted and kneaded to form a malleable putty. The PBS is added in sufficient amount that water constitutes about 70% by weight of the formed putty. The putty formed is a malleable, cohesive, fibrous mass with entrained ceramic granules.

EXAMPLE 3

Preparation of Osteogenic Putty

A buffered aqueous solution of rhBMP-2 (1.5 mg/ml solution, as available with INFUSE® Bone Graft, Medtronic Sofamor Danek, Memphis, Tenn.) is added to the body of Example 1, and the body is disrupted and kneaded to form a malleable putty. The rhBMP-2 solution is added in sufficient amount that water constitutes about 70% by weight of the formed putty. The putty formed is an osteogenic, malleable, cohesive, fibrous mass with entrained ceramic granules.

EXAMPLE 4

Use of Inventive Putty in Interbody Spinal Fusions

An ovine interbody fusion model is used to compare the ability of a 5 mm×11 mm×11 mm polyetheretherketone spinal spacer (VERTE-STACK® CORNERSTONE® PSR PEEK Implant, Medtronic Sofamor Danek, Memphis, Tenn.) with packed-in Autograft and the PEEK spacer with packed-in Osteogenic Putty of Example 3 to effect interbody fusion at 6 months post-operatively. The efficacy of these treatments to induce interbody fusion in the ovine lumbar fusion model using blinded radiographic, biomechanical, and histologic measures is evaluated. Assessment of fusion is made with Faxitron high-resolution radiography, non-destructive biomechanical testing, and undecalcified histology with corresponding microradiography. All analyses are conducted in a blinded fashion. In addition, undecalcified histology is used to evaluate the osteocompatibility of the Example 3 Putty. In addition to the treatment groups being evaluated, normal spines are evaluated using the same methodology. When all data acquisition is complete, the key is broken, and radiographic, biomechanical, and histologic data are analyzed by treatment group.

Animal Model:

The sheep lumbar spine model is used because of the biomechanical similarities between the sheep and human lumbar spine. Wilke et al. characterized the biomechanical parameters (range of motion, neutral zone, and level stiffness) of sheep spines and made comparisons with data from human specimens previously published by White and Panjabi (see, Wilke et al., *Spine:* 22(20): 2365-2374, 1997; and White A A and Panjabi M M, editors, Clinical Biomechanics of the Spine, 2nd ed., J. B. Lippincott, Philadelphia, Pa., 1990). Wilke et al. found that the "ranges of motion of sheep spines for the different load directions are qualitatively similar in their craniocaudal trends to those of human specimens reported in the literature." They further concluded that: "Based on the biomechanical similarities of the sheep and human spines demonstrated in this study, it appears that the sheep spine . . . can serve as an alternative for the evaluation of spinal implants.

Surgical Technique:

Upon arrival at the facility, the 12 sheep are placed in the appropriate pastures of the large animal research barn. They are dewormed and eartagged for identification. Physical examination is performed and any animals with signs of respiratory disease had venous blood submitted for a complete blood count (CBC).

The sheep are anesthetized. Wool is removed from the dorsal lumbar area and the sheep positioned in sternal recumbency on the operating table.

Iliac Crest Autoaraft Harvesting:

Autograft is used as a control. The following protocol is followed. The dorsal and dorsolateral lumbar and iliac crest areas are prepared for aseptic surgery with multiple scrubs of povidone-iodine alternated with isopropyl alcohol. The area is draped and a 3-cm incision made over the left iliac crest. Following partial reflection of the gluteal muscles, an osteotome is used to create a small window in the craniodorsal face of the iliac crest. Using a curette, about 2 cc of autogenous cancellous bone is removed, and is later packed into one of the implants (e.g. PEEK spacer) used for the lumbar fusion (this is the control case). Intralesional morphine sulfate is administered prior to closure of the iliac crest incision. The iliac crest site is closed routinely using 2/0 polysorb for the subcutaneous tissues and stainless steel staples for the skin.

Ventral ("Anterior") Interbody Fusion:

The dorsal and dorsolateral lumbar area is prepared for aseptic surgery with multiple scrubs of povidone-iodine alternated with isopropyl alcohol. The area is draped and a ventrolateral retroperitoneal approach to L3/L4 and L5/L6 through the oblique abdominal muscles to the plane ventral to the transverse processes is made.

Implant Insertion:

The bone graft from the iliac crest or the Example 3 Putty is placed into the PEEK spacer (~1.5 cc of material) and implanted into the disc space, following preparation of the endplates.

Wound Closure:

Routine closure of external abdominal muscular fascia (0 Polysorb (absorbable suture), subcutaneous tissue (2/0 Polysorb and skin (2/0 monofilament non-absorbable suture) is performed. Operative time for each animal is about 40 minutes. Perioperative antibiotics (Cephazolin sodium) are administered. Postoperative radiographs are performed while the sheep are still under general anesthesia.

Aftercare:

Immediately after surgery, the sheep are transferred from the operating table to a modified wheelbarrow and while still under general anesthesia, taken to a radiology suite where dorsoventral and lateral radiographs of the fusion sites are obtained. Following radiographic evaluation, while still in the modified wheelbarrow, they are observed until the swallowing reflex returns. At that point they are extubated and taken to a trailer where they are propped in sternal recumbency. At the end of the day, all animals that are operated upon that day are moved to research pastures. The sheep are housed outdoors (with access to a three-sided shelter) for the convalescence and allowed to exercise at will. Postoperative analgesia is provided as described. The sheep are anesthetized and radiographed at three months posoperatively.

Euthanasia:

After 6 months postoperatively, the 12 sheep are euthanized in a humane manner. Euthanasia is performed according to the guidelines set forth by the AVMA Panel on Euthanasia (J. Am. Vet. Med. Assoc., 202:229-249, 1993). Radiographs of the lumbar fusion sire are taken in these sheep to evaluate the degree of fusion at L3-L4.

Specimen Collection and Handling:

Following euthanasia, a complete gross necropsy is conducted on all 12 animals. Conventional gross examination of all major organ systems and histopathological evaluation of any pathological lesions is performed. Any animals that die or are prematurely euthanized during the course of the study have a complete necropsy performed to determine the cause of disease or death. At necropsy the lumbar vertebrae that are fused are harvested.

Material Analysis:

All samples from the lumbar area from the sheep are subjected to mechanical testing of the fusion sites. They are tested for stiffness to saggital and coronal plan bending moments (flexion, extension, right and left lateral bending). As these mechanical tests are nondestructive, the fusion sites are also examined histologically.

Implant Materials:

Twelve treated spinal levels (L4-L5) are evaluated. The study groups are defined below.

| Study Group | No. of Samples (N) |
|---|---|
| Autograft Interbody w/PEEK spacer (Autograft + PEEK) | 6 |
| Example 3 Putty w/PEEK spacer | 6 |
| Normal Intact | 17 |
| Total | 29 |

After the survival phase of the study is completed, the spines are immediately frozen for evaluation.

Methods of Analysis:

1. Ex-vivo Biomechanical Testing of the Treated Lumbar Motion Segment:

Flexibility Testing

Unconstrained biomechanical testing is performed in a non-destructive manner on all spines after the frozen specimens are thawed. All tests are performed within 12 hours of specimen thawing. Specimens are only frozen once. Instrumentation applied to the anterior part of the vertebral body is removed prior to biomechanical testing so that only the stiffness of the spine and fusion mass construct is tested, not the instrumentation. Flexibility of the motion segments is determined in flexion, extension, right and left lateral bending, and right and left axial rotation. The purpose of the biomechanical testing is to quantify the stiffness of the lumbar motion segments augmented with the previously described interbody fusion treatments. The treated (L4-L5) motion segments are dissected from the harvested lumbar spines and cleaned of extraneous soft tissues leaving the ligamentous and osseous tissues intact. Specially designed loading and base frames are secured on the L4 and L5 vertebra, respectively.

Moments of 0, 0.5, 2.5, 4.5, 6.5, and 8.5 Nm are achieved in each loading direction. Static loads are used to apply the pure moments. Three markers reflecting the infrared light are attached to each vertebra. The locations of the infrared reflective markers are recorded using three VICON cameras (ViconPeak, Oxford, England) at each load. Three-dimensional load-displacement data are then acquired with pure moments applied in flexion, extension, left and right lateral bending, and left and right axial rotation. Basic principles of using 3-D motion analysis system for investigating the 3-D load-displacement behavior are well known in the literature.

Biomechanics data from a normal (untreated) intact group of sheep lumbar spine motion segments that have been obtained previously are used as baseline data for normal lumbar spine motion for L4-L5 in sheep. Differences in the stiffness (flexibility) between groups and the normals are statistically compared. Non-parametric Kruskal-Wallis and Mann-Whitney tests are used to analyze the biomechanics data.

2. Radiographic Assessment:

Radiographs are taken immediately after surgery (AP and lateral views), at regular post-operative intervals (AP and lateral views), and at the time of sacrifice (AP and lateral views). A high-resolution radiography unit (Faxitron, Hewlett Packard, McMinnville, Oreg.) and high-resolution film (EKTASCAN B/RA Film 4153, Kodak, Rochester, N.Y.) are used to produce a high-resolution PA and lateral radiograph of the harvested lumbar spines after biomechanical testing. Radiographs are scanned using image analysis software (Image Pro Plus Software v 5.0, Media Cybernetics, Silver Spring, Md.) running on a Windows XP workstation. A video camera (Model DFC 280, Leica Microsystems, Cambridge, UK) is used to acquire the digital images of the radiographs. These radiographs are also used to gross the samples for histologic analyses as outlined below.

Three blinded evaluators evaluate the resulting Faxitron radiographs for interbody fusion. On the lateral radiographs, the center of the disc space as well as the anterior and posterior margins are evaluated for fusion based on the following scoring method: 4=continuous bony bridging, 3=increased bone density, 2=lucency with some bony bridging, and 1=non-fusion. Lastly, based on both the P/A and lateral radiographs, the blinded evaluators rate an overall fusion score for the spinal level using the following criteria:

3 = Solid interbody fusion with no radiolucencies in interbody space
2 = Probable fusion with radiolucencies in the interbody space
1 = Non-fusion with significant radiolucencies in the disc space with no evidence of superior to inferior bony bridging 3. Undecalcified Histology and Microradiography:

Processing and Stained Undecalcified Sections

In all of the treatment groups, the bisected spinal level is analyzed using undecalcified techniques (microradiographs and multiple stain). Differential staining along with qualitative optical microscopy is performed to assess bony bridging and extent of fusion associated with the autograft or the bone graft substitute packed within the PEEK spacers. Differential staining is used to evaluate the extent of fusion adjacent to and within the PEEK spacers, the host response to the PEEK spacer and Example 3 Putty (if present), the interface of the PEEK spacer, bone graft and Example 3 Putty incorporation, and bone remodeling within the fusion mass.

After Faxitron radiography, all spinal levels containing an implant are grossed in the following manner. Using the band saw, a coronal plane cut is made along the entire length of the spinal column at the anterior aspect of the pedicles leaving anterior tissues intact. Tissues posterior to the disc space are discarded. Next, the anterior column of the spinal level is bisected mid-sagittally to produce right and left halves. The entire disc space is left intact. The inferior half of the L4 anterior column adjacent to the treated level is retained. The superior half of the L5 anterior column adjacent to the treated level is retained. Right and left sagittal samples from the level are so labeled, fixed in formalin, and processed (sequentially dehydrated in alcohols, cleared in a xylene substitute, and embedded in graded catalyzed methyl methacrylate.

After polymerization is complete and the samples hardened, sectioning and staining is performed. The blocks containing the right and left halves of the treated aspect of the spinal level are sectioned in the sagittal plane on a low speed diamond saw (Buehler Isomet, Lake Bluff, Ill.). For all embedded tissue blocks, sagittal sectioning commence from the middle of the treated aspect of the spinal level to the lateral aspect of the treated area. Thus, section #1 from the "right block" is sampled in the middle of the fusion mass whereas section #6 from the "right block" is sampled at the far lateral aspect of the treated area. Weights are used to produce sections on the order of 300 µm. Approximately 5-10 sections are made in the sagittal plane through each half of the interbody space. If necessary, grinding is performed to obtain the desired thickness. The thickness of the sections is measured with a metric micrometer (Fowler, Japan). Differential staining using a trichrome stain is used to permit histological differentiation.

Stained undecalcified sections are scanned using image analysis software (Image Pro Plus Software v 5.0, Media Cybernetics, Silver Spring, Md.) running on a Windows XP workstation. A video camera (Model DFC 280, Leica Microsystems, Cambridge, UK) is used to acquire the digital images of the stained undecalcified sections.

Section Fusion Criteria:

Undecalcified sections are evaluated for fusion in the center of the disc space or thrugrowth region of the device, in the anterior margin, and in the posterior margin. These anatomic locations for each section are considered to be fused only if continuous bony bridging is found from superior to inferior.

Level Fusion Criteria:

Based on all sections evaluated, the following criteria are used to determine if histologic fusion is present in the level. The spinal level is considered fused if greater than 50% of the sections (corresponding microradiographs are analyzed concurrently but not "counted twice" for fusion) show continuous bony bridging. A partial fusion exists if less than 50% of the sections (and corresponding microradiographs) show continuous bony bridging. A non-fusion exists if none of the sections and corresponding microradiographs show continuous bony bridging.

Microradiography

Undecalcified sections from the treated lumbar spinal levels are radiographed using a microradiography unit (Faxitron radiography unit, Hewlett Packard, McMinnville, Oreg.) and spectroscopic film (B/RA 4153 film, Kodak, Rochester, N.Y.). The thickness of the sections is measured with a metric micrometer (Fowler, Japan) to determine the exposure time. Sections are labeled with ultra-fine permanent markers, placed on the Ektascan B/RA 4153 film, and exposed to the x-ray source at 20 kV and 3 mA for approximately 45 seconds for each 100 µm of section thickness. The film is then developed, fixed, and analyzed for ossification using standard optical microscopy. Microradiographs are scanned using image analysis software (Image Pro Plus Software v 5.0, Media Cybernetics, Silver Spring, Md.) running on a Windows XP workstation. A video camera (Model DFC 280, Leica Microsystems, Cambridge, UK) is used to acquire the digital images of the microradiographs.

Analysis of the sections and microradiographs is used to:
1) Evaluate the extent of fusion adjacent to and within the PEEK spacers, bone graft and Example 3 Putty incorporation, and bone remodeling within the fusion mass,
2) Determine the host response to the biomaterials used, and
3) Evaluate the interface of the PEEK spacer.

EXAMPLE 5

Use of Osteogenic Putty in Posterolateral Fusion

An instrumented ovine posterolateral fusion model is used to evaluate the ability of Autograft and the Osteogenic Putty of Example 3 to effect posterolateral fusion at 6 months post-operatively. The efficacy of these treatments to induce posterolateral fusion in the ovine lumbar fusion model is evaluated using blinded radiographic, biomechanical, and histologic measures. Assessment of fusion is made with Faxitron high-resolution radiography, non-destructive biomechanical testing, and undecalcified histology with microradiography. All analyses are conducted in a blinded fashion. In addition, undecalcified histology is used to evaluate the osteocompatibility of the osteogenic putty. In addition to the treatment groups being evaluated, biomechanical properties of normal spines are evaluated using the same methodology. When all data acquisition is complete, the key is broken, and radiographic, biomechanic, and histologic data are analyzed by treatment group.

Animal Model:

The sheep lumbar spine model is used because of the biomechanical similarities between the sheep and human lumbar spine. Wilke et al. characterized the biomechanical parameters (range of motion, neutral zone, and level stiffness) of sheep spines and made comparisons with data from human specimens previously published by White and Panjabi (see, Wilke et al., Spine: 22(20): 2365-2374, 1997; and White A A and Panjabi M M, editors, Clinical Biomechanics of the Spine, 2nd ed., J. B. Lippincott, Philadelphia, Pa., 1990). Wilke et al. found that the "ranges of motion of sheep spines for the different load directions are qualitatively similar in their craniocaudal trends to those of human specimens reported in the literature." They further concluded that: "Based on the biomechanical similarities of the sheep and human spines demonstrated in this study, it appears that the sheep spine . . . can serve as an alternative for the evaluation of spinal implants.

Surgical Technique:

12 sheep are placed in the appropriate pastures of the large animal research barn. They are dewormed and eartagged for identification. Physical examination is performed and any animals with signs of respiratory disease have venous blood submitted for a complete blood count (CBC).

The sheep are anesthetized. Wool is removed from the dorsal lumbar area and the sheep positioned in sternal recumbency on the operating table. The dorsal and dorsolateral lumbar area are prepared for aseptic surgery with multiple scrubs of povidone-iodine alternated with isopropyl alcohol. The area is draped and a dorsal approach to L3-L6 is made through the dorsal lumbar musculature.

Iliac Crest Autograft Harvesting:

Autograft is used as a control. The following protocol is followed. The dorsal and dorsolateral lumbar and iliac crest areas are prepared for aseptic surgery with multiple scrubs of povidone-iodine alternated with isopropyl alcohol. The area is draped and a 3-cm incision made over the left iliac crest. Following partial reflection of the gluteal muscles, an osteotome is used to create a small window in the craniodorsal face of the iliac crest. Using a curette, about 2 cc of autogenous cancellous bone is removed, and is later packed into one of the implants (e.g. PEEK spacer) used for the lumbar fusion (this is the control case). Intralesional morphine sulfate is administered prior to closure of the iliac crest incision. The iliac crest site is closed routinely using 2/0 polysorb for the subcutaneous tissues and stainless steel staples for the skin.

Dorsolateral ("posterolateral") Interbody Fusion:

The dorsal lumbar area is prepared for aseptic surgery with multiple scrubs of povidone-iodine alternated with isopropyl alcohol. The area is draped and local anesthesia (Bupivicaine) is infiltrated along the site of the intended incision for the dorsal approach to L3 and L4 and spinous processes.

Approach to the Transverse Processes:

A 20 cm. skin incision is made and the paraspinal muscles are dissected off the spinous processes and laminae. Facet joints and transverse processes between L3 and L4 are exposed.

Instrumentation and Spine Fusion Technique:

The transverse processes of L3 and L4 are decorticated bilaterally. The bone graft from the iliac crest or the osteogenic putty of Example 3 is placed between the transverse processes (~10 cc per side). The sheep now undergoes transpedicular screw fixation using screws and rods. The pedicle screws and rods are inserted at this point in the procedure.

Wound Closure:

Routine closure of external abdominal muscular fascia (0 Polysorb (absorbable suture), subcutaneous tissue (2/0

Polysorb and skin (2/0 monofilament non-absorbable suture) is performed. Operative time for each animal is about 50 minutes. Perioperative antibiotics (Cephazolin sodium) are administered. Postoperative radiographs are performed while the sheep are still under general anesthesia.

Aftercare:

Immediately after surgery, the sheep are transferred from the operating table to a modified wheelbarrow and while still under general anesthesia, and taken to a radiology suite where dorsoventral and lateral radiographs of the fusion sites are obtained. Following radiographic evaluation, while still in the modified wheelbarrow, they are observed until the swallowing reflex returns. At that point they are extubated and taken to a trailer where they are propped in sternal recumbency. At the end of the day, all animals that are operated upon that day are moved to research pastures. The sheep are housed outdoors (with access to a three-sided shelter) for the convalescence and allowed to exercise at will. Postoperative analgesia is provided as described. The sheep are anesthetized and radiographed at three months posoperatively.

Euthanasia:

After 6 months postoperatively, the 12 sheep are euthanized in a humane manner. Euthanasia is performed according to the guidelines set forth by the AVMA Panel on Euthanasia (J. Am. Vet. Med. Assoc., 202:229-249, 1993). Radiographs of the lumbar fusion sire are taken in these sheep to evaluate the degree of fusion at L3-L4.

Specimen Collection and Handling:

Following euthanasia, a complete gross necropsy is conducted on all 12 animals. Conventional gross examination of all major organ systems and histopathological evaluation of any pathological lesions is performed. Any animals that died or were prematurely euthanized during the course of the study have a complete necropsy performed to determine the cause of disease or death. At necropsy the lumbar vertebrae that are fused are harvested.

Material Analysis:

All samples from the lumbar area from the sheep are subjected to mechanical testing of the fusion sites. They are tested for stiffness to saggital and coronal plan bending moments (flexion, extension, right and left lateral bending). As these mechanical tests are nondestructive, the fusion sites are also examined histologically.

Implant Materials:

The study groups are defined below.

| Study Group (per study design) | No. of Samples (N) |
| --- | --- |
| 1) 10 cc/side Autograft (Autograft) | 6 |
| 2) Example 3 Putty | 6 |
| 3) Normal Intact | 17 |
| Total | 28 |

At the completion of the survival phase of the animal study, the spines are immediately frozen for evaluation. The efficacy of the bone graft and bone graft substitutes to effect posterolateral fusion and bony healing is assessed by performing radiographic, biomechanical, and histologic analyses as detailed below. The study is performed in a blinded fashion. After all analyses are completed, the key is broken and radiographic, biomechanical, and histologic data are analyzed by treatment group.

Methods of Analysis:

1. Radiographic Assessment:

Radiographs are taken immediately after surgery, at regular post-operative intervals, and at the time of sacrifice. A Faxitron (Hewlett Packard, McMinnville, Oreg.) high-resolution radiography unit and high-resolution film (EKTASCAN B/RA Film 4153, Kodak, Rochester, N.Y.) is used to produce a high-resolution PA radiograph of the harvested lumbar spines after biomechanical testing. Radiographs are scanned using image analysis software (Image Pro Plus Software v 5.0, Media Cybernetics, Silver Spring, Md.) running on a Windows XP workstation. A video camera (Model DFC 280, Leica Microsystems, Cambridge, UK) is used to acquire the digital images of the radiographs. These radiographs are also used to gross the samples for histologic analyses as outlined below.

Three blinded evaluators evaluate the resulting Faxitron radiographs for intertransverse process fusion. On the PA radiograph, on both the right and left sides of the level, the intertransverse process space is evaluated for fusion based on the following scoring method: 4=continuous bony bridging, 3=increased bone density, 2=lucency with some bony bridging, and 1=non-fusion. Based on both the right and left sides of the PA radiographs, the blinded evaluators rate an overall fusion score for the spinal level using the following criteria:

| | |
| --- | --- |
| 3 = | Solid Fusion: Solid intertransverse process fusion on Right AND Left with no radiolucencies |
| 2 = | Possible Fusion: Intertransverse process fusion on the Right OR Left, but not both. Lucencies in intertransverse process space on right or left. |
| 1 = | Non-Fusion: Isolated bone formation without continuous superior to inferior bony bridging on both right and left sides. Significant lucency with no evidence of intertransverse process fusion on the right or left. |

After the treatment code is broken, the radiographic fusion data are statistically analyzed.

2. Ex-vivo Biomechanical Testing of the Treated Lumbar Motion Segment:

Flexibility Testing:

Unconstrained biomechanical testing is performed in a non-destructive manner on all spines after the frozen specimens are thawed. All metallic posterior instrumentation used to stabilize the posterolateral fusion is removed prior to biomechanical testing so that the stiffness of the spine and fusion mass construct is tested. Flexibility of the motion segments is determined in flexion, extension, right and left lateral bending, and right and left axial rotation. All tests are performed within 12 hours of specimen thawing. Specimens are only frozen once. The purpose of the biomechanical testing is to quantify the stiffness of the lumbar motion segments augmented with the previously described fusion treatments. The treated (L4-L5) motion segments are dissected from the harvested lumbar spines and cleaned of extraneous soft tissue leaving the ligamentous and osseous tissues intact. Specially designed loading and base frames are secured on the L4 and L5 vertebra, respectively.

Moments of 0, 0.5, 2.5, 4.5, 6.5, and 8.5 Nm are achieved in each loading direction. Static loads are used to apply the pure moments. A six-degree of freedom load cell is placed in series with the tested specimen to verify the applied moments. Three markers reflecting the infrared light are attached to each vertebra. The locations of the infrared reflective markers are recorded using three VICON cameras (Vicon Peak, Oxford, England) at each load. Three-dimensional load-displacement data are then acquired with pure moments applied in flexion, extension, left and right lateral bending, and left and right axial rotation. The three-dimensional coordinate data are analyzed to obtain the rotation angles of the superior vertebra with respect to the inferior vertebra and rotational flexibility of each motion segment.

Biomechanics data from a normal (untreated) intact group of sheep lumbar spine motion segments that have been obtained previously are used as baseline data for normal lumbar spine motion for L4-L5 in sheep. Differences in the stiffness (flexibility) between groups and the normals are statistically compared. Non-parametric Kruskal-Wallis and Mann-Whitney tests are used to analyze the biomechanics data.

3. Undecalcified Histology and Microradiography:

Processing and Stained Undecalcified Sections: In each of the treatment groups, the bisected spinal intertransverse process spaces are analyzed using undecalcified techniques (microradiographs and multiple stain). Differential staining along with qualitative optical microscopy is performed to assess bony bridging and extent of fusion associated with autograft and the osteogenic putty of Example 3.

After Faxitron radiography, all spinal levels containing an implant are grossed in the following manner. The superior (L3-L4) and inferior (L5-L6) disc spaces are transected leaving the treated (L4-L5) functional spinal unit (FSU) intact. Using the band saw, a coronal plane cut is made along the entire length of the spinal column at the anterior aspect of the pedicles leaving posterior tissues intact. Anterior tissues are discarded. Next, the posterior elements of the spinal level are bisected mid-sagittally to produce right and left halves. An angled cut in the axial plane is made so that tissues cranial to the cranial transverse processes are discarded on the right and left sides. An angled cut in the axial plane is made so that tissues caudal to the caudal transverse processes are trimmed and discarded on the right and left sides. Tissues in the Right and Left intertransverse process spaces are further divided in the sagittal plane to produce a medial and lateral sample of the Left fusion mass as well as a medial and lateral sample of the Right fusion mass. Right and left medial and lateral samples are so labeled, fixed in formalin, and processed (sequentially dehydrated in alcohols, cleared in xylene or xylene substitute, and embedded in graded catalyzed methyl methacrylate).

After polymerization is complete and the samples hardened, sectioning and staining is performed. The blocks containing the transverse processes, autograft and Example 3 putty, and tissues in the transverse process space are sectioned in the sagittal plane on a low speed diamond saw (Buehler Isomet, Lake Bluff, Ill.). For the medial and lateral embedded tissue blocks described above, sectioning commences from the middle of the fusion mass for both the medial and lateral blocks. Thus, section #1 from the "right lateral block" is sampled in the middle of the fusion mass whereas section #6 from the "right lateral block" is sampled at the far lateral anatomic aspect of the fusion mass (tips of the transverse processes). Similarly, section #1 from the "right medial block" is sampled in the middle of the fusion mass whereas section #6 from the "right medial block" is sampled at the far medial anatomic aspect of the fusion mass (lamina and facet joints). Weights are used to produce sections on the order of 300 μm. Approximately 5-10 sections are made in the sagittal plane through each half of the intertransverse process space. If necessary, grinding is performed to obtain the desired thickness. The thickness of the sections is measured with a metric micrometer (Fowler, Japan). Differential staining using a trichrome stain is used to permit histological differentiation.

Stained undecalcified sections are scanned using image analysis software (Image Pro Plus Software v 5.0, Media Cybernetics, Silver Spring, Md.) running on a Windows XP workstation. A video camera (Model DFC 280, Leica Microsystems, Cambridge, UK) is used to acquire the digital images of the stained undecalcified sections. Undecalcified histology sections and microradiographs for this study are scanned so that dorsal is at the top of the image. The ventral side of the section is usually flat and shows two oval transverse processes. Sections are scanned so that transverse processes are at the bottom (ventral aspect) of the image. A mm scale is scanned at the bottom (ventral aspect) of the image. Microsoft Photo editor is used to crop the images.

Section Fusion Criteria:

Undecalcified sections are considered fused if continuous bony bridging is found from superior to inferior in the section. If the presence of non-osseous tissues obviated continuous bony bridging, the section is further evaluated as follows. For non-fused sections, sections are classified as A) non-fusion with incomplete bridge, but with de novo bone found in >50% of the length of the section, or B) non-fusion with incomplete bridge, with de novo bone found in <50% of the length of the section.

Right and Left Side Level Fusion Criteria:

Based on all sections evaluated, the following criteria are used to determine if histologic fusion is present on the right or left side of the level. The right or left side of the spinal level is considered fused if greater than 50% (>50%) of the sections and corresponding microradiographs show continuous bony bridging. A partial fusion exists if 50% or less (<50%) of the sections and corresponding microradiographs from the right or left side of the spinal level show continuous bony bridging. A non-fusion exists if none of the sections and corresponding microradiographs from the right or left side of the spinal level shows continuous bony bridging.

Microradiography:

Undecalcified sections from the treated lumbar spinal levels are radiographed using a microradiography unit (Faxitron radiography unit, Hewlett Packard, McMinnville, Oreg.) and spectroscopic film (B/RA 4153 film, Kodak, Rochester, N.Y.). The thickness of the sections is measured with a metric micrometer (Fowler, Japan) to determine the exposure time. Sections are labeled with ultra-fine permanent markers, placed on the Ektascan B/RA 4153 film, and exposed to the x-ray source at 20 kV and 3 mA for approximately 45 seconds for each 100 μm of section thickness. The film is then developed, fixed, and analyzed for ossification using standard optical microscopy. Microradiographs are scanned using image analysis software (Image Pro Plus Software v 5.0, Media Cybernetics, Silver Spring, Md.) running on a Windows XP workstation. A video camera (Model DFC 280, Leica Microsystems, Cambridge, UK) is used to acquire the digital images of the microradiographs.

Analysis of the sections and microradiographs is used to:
1) Evaluate histologic fusion,
2) Determine the host response to the autograft and bone graft substitutes, and
3) Estimate the quality and quantity of bone in the fusion mass within the intertransverse process space.

The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all references cited herein are indicative of the level of skill in the art and are hereby incorporated by reference in their entirety.

What is claimed is:

1. A medical implant composition, comprising:
   a malleable mechanically entangled mass of elongate, compliant noncollagenous scaffolding elements composed of one or more synthetic polymers, forming a loaded scaffolding material, the mechanically entangled mass having an osteoconductive calcium-containing particulate material incorporated therein, said scaffolding material comprising between 11% by weight of said composition and 50% by weight of said composition;
   a biodegradable barrier substance coating the exterior surface of the loaded scaffolding material;
   sulfated glycosaminoglycan molecules bound to said scaffolding elements; and
   a liquid organic binder coating said scaffolding elements comprising an aqueous medium comprising an alginate polymer having an average molecular weight ranging from 2 to 100 kD and more than 50% alpha-L-guluronic acid, said liquid organic binder having a viscosity in a range from about 1 centipoise to about 200 centipoises and being present in an amount that is effective to increase the cohesivity of said mechanically entangled mass,
   wherein said liquid organic binder comprises about 60% to about 75% by total weight of said composition.

2. The composition of claim 1, wherein said scaffolding elements comprise ribbons having a median width in the range of about 0.2 mm to about 3 mm, a median length in the range of about 5 mm to about 20 mm, and a median thickness in the range of about 0.02 mm to about 0.2 mm.

3. The osteoinductive composition of claim 1, wherein bone morphogenic protein is incorporated into said composition at a level of about 0.6 mg/cc of said composition to about 2.0 mg/cc of said composition, wherein said bone morphogenic protein comprises recombinant human BMP-2.

4. The osteoinductive composition of claim 2, wherein the bioresorbable ribbons are present in said composition at a level of about 0.05 g/cc to about 0.08 g/cc.

5. The osteoinductive composition of claim 2, wherein said calcium-containing particulate material comprises biphasic calcium phosphate.

6. The osteoinductive composition of claim 1, wherein said scaffolding elements comprise a synthetic bioresorbable polymer or a bioresorbable silk, and wherein said composition is free from animal-derived protein.

7. The osteoinductive composition of claim 2, wherein said sulfated glycosaminoglycan comprises heparin.

8. An osteoinductive composition, comprising:
   a malleable mechanically entangled mass of elongate, compliant scaffolding elements, wherein said scaffolding elements are composed of (i) one or more synthetic polymers, (ii) one or more plant-derived biopolymers, (iii) one or more insect-derived biopolymers, or (iv) mixtures including two or all of (i), (ii) and (iii), forming a loaded scaffolding material, said loaded scaffolding material comprising between 11% by weight of said composition and 50% by weight of said composition;
   a biodegradable barrier substance coating the exterior surface of the loaded scaffolding material;
   a liquid organic binder coating said scaffolding elements comprising an aqueous medium comprising an alginate polymer having an average molecular weight ranging from 2 to 100 kD and more than 50% alpha-L-guluronic acid, said liquid organic binder having a viscosity in a range from about 1 centipoise to about 200 centipoises and comprising about 60% to about 75% by weight of said composition so as to be effective to increase the cohesivity of said mechanically entangled mass;
   an osteoinductive factor incorporated in said mechanically entangled mass, said osteoinductive factor comprising bone morphogenic protein incorporated into said composition at a level of about 0.6 mg/cc of said composition to about 2.0 mg/cc of said composition; and
   wherein said scaffolding elements exhibit a capacity to bind said osteoinductive factor.

9. The composition of claim 8, wherein said scaffolding elements comprise ribbons.

10. A noncollagenous osteoinductive material for implantation to induce bone growth in a patient, comprising:
    an osteoinductive implant material comprising an osteoconductive scaffolding material incorporating an osteoinductive protein and one or more synthetic polymers, said osteoinductive protein comprising bone morphogenic protein incorporated into said osteoinductive material at a level of about 0.6 mg/cc of said osteoinductive material to about 2.0 mg/cc of said osteoinductive material, said osteoconductive scaffolding material comprising between 11% by weight of said osteoinductive material and 50% by weight of said osteoinductive material;
    a liquid organic binder coating said scaffolding material comprising an aqueous medium comprising an alginate polymer having an average molecular weight ranging from 2 to 100 kD and more than 50% alpha-L-guluronic acid, said liquid organic binder having a viscosity in a range from about 1 centipoise to about 200 centipoises, said liquid organic binder comprising about 60% to about 75% by weight of said osteoinductive material; and
    a coating upon exterior surfaces of the osteoinductive implant material, the coating including a biodegradable barrier substance and being effective to delay release of the osteoinductive protein from the scaffolding material.

11. The composition of claim 1, wherein said alginate polymer has a viscosity of 25 to 1000 mPas in a 1% solution measured at 20° C.

12. The composition of claim 1, wherein said alginate polymer has an average molecular weight from 5 to 350 kD, from 2 to 100 kD, from 50 to 500 kD, or from 100 to 1000 kD.

13. The composition of claim 1, wherein said alginate polymer comprises 60-80% alpha-L-guluronic acid.

14. The composition of claim 1, wherein:
bone morphogenic protein is incorporated into said composition at a level of about 0.6 mg/cc of said composition to about 2.0 mg/cc of said composition
said osteoconductive calcium-containing material is incorporated at a level of about 0.25 g/cc of the composition to about 0.35 g/cc of the composition; and
said osteoconductive calcium-containing material comprises about 70% to about 90% by dry weight of the composition.

15. The composition of claim 2, wherein said osteoconductive calcium-containing material comprises about 70% to about 90% by dry weight of the composition.

16. The composition of claim 1, wherein said scaffolding material comprises 15% by weight of said composition.

17. The composition of claim 1, further comprising a crosslinking agent.

18. The composition of claim 1, further comprising a crosslinking agent comprising calcium chloride.

19. The composition of claim 1, wherein said scaffolding material comprises bioresorbable ribbons.

20. The composition of claim 1, wherein said scaffolding material comprises bioresorbable ribbons, said ribbons being configured to be resorbed within about four to about six weeks after implantation of said composition.

21. The composition of claim 1, wherein said osteoconductive calcium-containing particulate material comprises a tricalcium phosphate:hydroxyapatite weight ratio of about 50:50 to about 95:5.

22. The composition of claim 1, wherein said composition is dried to form an implant having a porosity of greater than 50%.

23. The composition of claim 1, wherein said composition is dried to form an implant having a porosity in a range of about 80% to about 90%.

24. The composition of claim 1, wherein said alginate polymer comprises 0.01 g/cc to 0.08 g/cc of said composition.

25. The composition of claim 1, wherein said scaffolding elements comprise intermeshed ribbons.

* * * * *